United States Patent [19]
Williamson et al.

[11] Patent Number: 5,951,799
[45] Date of Patent: Sep. 14, 1999

[54] ANTI-MICROBIAL SHOE LINING AND SOCK LINER AND PROCESS FOR MANUFACTURE OF SAME

[75] Inventors: Robert R. Williamson; Norwin C. Derby, both of Dallas; Craig Alan Nickell, Sherman, all of Tex.

[73] Assignee: Super Sack Manufacturing Corp., Dallas, Tex.

[21] Appl. No.: 08/840,791

[22] Filed: Apr. 16, 1997

Related U.S. Application Data

[63] Continuation-in-part of application No. 08/474,378, Jun. 7, 1995, abandoned.

[51] Int. Cl.$^6$ ............................ A43B 13/38; A43B 23/07
[52] U.S. Cl. ................................ 156/148; 36/43; 36/55; 156/244.19
[58] Field of Search .............................. 156/148, 244.11, 156/244.19; 36/43, 55

[56] References Cited

U.S. PATENT DOCUMENTS

| | | |
|---|---|---|
| 546,168 | 9/1895 | Lobdell . |
| 616,249 | 12/1898 | Nickerson . |
| 733,542 | 7/1903 | Converse . |
| 1,355,607 | 10/1920 | Janicki . |
| 1,815,106 | 7/1931 | Jostes . |
| 2,009,511 | 7/1935 | Nydegger . |
| 2,047,095 | 7/1936 | Booth . |
| 2,096,161 | 10/1937 | Curran . |
| 2,301,128 | 11/1942 | Landefeld . |
| 2,314,876 | 3/1943 | Greene . |
| 2,361,943 | 11/1944 | Issoglio . |
| 2,507,939 | 5/1950 | Smith . |
| 2,691,998 | 10/1954 | Stucker . |
| 2,740,445 | 4/1956 | Fornell . |
| 2,969,102 | 1/1961 | Cunningham . |
| 3,044,438 | 7/1962 | Osswald et al. . |
| 3,072,512 | 1/1963 | Dalle . |
| 3,096,013 | 7/1963 | Kugler . |
| 3,282,757 | 11/1966 | Brussee . |
| 3,328,226 | 6/1967 | Wiley . |
| 3,351,365 | 11/1967 | Bick . |
| 3,374,929 | 3/1968 | Silfverskiold . |
| 3,430,815 | 3/1969 | Weimer et al. . |
| 3,445,055 | 5/1969 | Port . |
| 3,531,365 | 9/1970 | Melin . |
| 3,540,356 | 11/1970 | Lecomte . |
| 3,555,170 | 1/1971 | Petzetakis . |
| 3,570,749 | 3/1971 | Sato et al. . |
| 3,581,883 | 6/1971 | Whitney . |
| 3,589,506 | 6/1971 | Ford et al. . |
| 3,596,134 | 7/1971 | Burke . |
| 3,596,824 | 8/1971 | Lemacher et al. . |
| 3,607,616 | 9/1971 | Barbehenn et al. . |
| 3,620,774 | 11/1971 | Ford et al. . |
| 3,623,937 | 11/1971 | Gasaway . |
| 3,636,185 | 1/1972 | Ruddell et al. . |
| 3,661,322 | 5/1972 | Norman . |
| 3,666,585 | 5/1972 | Barbehenn . |
| 3,671,383 | 6/1972 | Sakata et al. . |
| 3,701,559 | 10/1972 | Marino et al. . |
| 3,742,664 | 7/1973 | Reding . |
| 3,754,053 | 8/1973 | Kray et al. . |
| 3,754,063 | 8/1973 | Schirmer . |
| 3,789,897 | 2/1974 | Saito . |
| 3,798,115 | 3/1974 | Hoffman et al. . |
| 3,827,471 | 8/1974 | Gregory et al. . |
| 3,865,339 | 2/1975 | Von Alven . |
| 3,874,989 | 4/1975 | Stange et al. . |
| 3,893,595 | 7/1975 | Khanna et al. . |
| 3,907,955 | 9/1975 | Viennot . |
| 3,961,655 | 6/1976 | Nattrass et al. . |
| 3,982,986 | 9/1976 | Stone et al. . |
| 4,010,784 | 3/1977 | Nattrass et al. . |
| 4,081,011 | 3/1978 | Krause . |
| 4,107,452 | 8/1978 | Razvi . |
| 4,113,146 | 9/1978 | Williamson . |
| 4,143,796 | 3/1979 | Willaimson et al. . |
| 4,149,755 | 4/1979 | Handleman et al. . |
| 4,194,652 | 3/1980 | Williamson et al. . |
| 4,221,250 | 9/1980 | Manerba . |
| 4,224,970 | 9/1980 | Williamson et al. . |
| 4,230,763 | 10/1980 | Skolnick . |
| 4,457,456 | 7/1984 | Derby et al. . |
| 4,467,005 | 8/1984 | Pusch et al. . |
| 4,560,608 | 12/1985 | Pusch . |
| 4,597,102 | 6/1986 | Nattrass . |
| 4,621,012 | 11/1986 | Pusch . |
| 4,666,706 | 5/1987 | Farquharson et al. .................. 424/408 |
| 4,692,494 | 9/1987 | Sonenstein ................................ 525/57 |
| 4,759,473 | 7/1988 | Derby et al. . |

(List continued on next page.)

FOREIGN PATENT DOCUMENTS

| | | |
|---|---|---|
| 413476 | 11/1962 | Switzerland . |
| 0915999 | 1/1963 | United Kingdom . |
| 1097040 | 12/1967 | United Kingdom . |
| WO 82/03202 | 9/1982 | WIPO . |

OTHER PUBLICATIONS

*Versicon* Conductive Polymer, Product Data Sheet, 1996, 8 pgs.

Plastics Get Wired, Scientific American, Jul. 1995, pp. 2–7.

Olin Chemicals, *Biocides Technical Product Information*, 1996, pp. 1–6.

Microban Products Company, *Microban Brochure for the Food–Service Industry*, 1994, 18 pgs.

*Primary Examiner*—Daniel Stemmer
*Attorney, Agent, or Firm*—Michael A. O'Neil

[57] ABSTRACT

A method of manufacturing a shoe lining having anti-microbial properties. The method comprises providing a quantity of a thermoplastic resin including an inorganic zinc-based anti-microbial agent admixture having a predetermined microbial inhibition characteristic. This thermoplastic resin is blended with a polyethylene resin to form an anti-microbial feedstock. The anti-microbial feedstock is formed into relatively long, narrow, thin lengths of anti-microbial members. These members are woven into an anti-microbial fabric having predetermined microbial inhibition characteristics. This fabric is cut into a plurality of pieces in accordance with a predetermined pattern and the pieces are joined together thereby constructing the anti-microbial shoe lining.

12 Claims, 8 Drawing Sheets

U.S. PATENT DOCUMENTS

| | | | |
|---|---|---|---|
| 4,833,008 | 5/1989 | Derby . | |
| 4,865,855 | 9/1989 | Hansen et al. | 426/124 |
| 5,024,792 | 6/1991 | Havens . | |
| 5,071,699 | 12/1991 | Pappas . | |
| 5,092,883 | 3/1992 | Wurr . | |
| 5,094,847 | 3/1992 | Yazaki | 424/618 |
| 5,100,943 | 3/1992 | Katoh . | |
| 5,106,649 | 4/1992 | Spices . | |
| 5,114,984 | 5/1992 | Branch et al. | 521/121 |
| 5,151,122 | 9/1992 | Atsumi | 424/618 |
| 5,158,766 | 10/1992 | Greenwald et al. | 424/78.33 |
| 5,180,585 | 1/1993 | Jacobson et al. | 424/405 |
| 5,192,134 | 3/1993 | Polett . | |
| 5,244,281 | 9/1993 | Williamson et al. . | |
| 5,296,238 | 3/1994 | Sugiura et al. | 424/604 |
| 5,468,738 | 11/1995 | Okabayashi et al. | 514/63 |
| 5,527,570 | 6/1996 | Addeo et al. | 428/35.7 |
| 5,534,563 | 7/1996 | Lin et al. | 523/122 |
| 5,549,895 | 8/1996 | Lyon et al. | 424/115 |
| 5,554,373 | 9/1996 | Seabrook | 424/400 |
| 5,554,673 | 9/1996 | Shah | 524/104 |
| 5,560,227 | 10/1996 | Depoe | 66/196 |
| 5,586,643 | 12/1996 | Zabron | 198/853 |

ANTI-MICROBIAL SHOE LINING AND SOCK LINER AND PROCESS FOR MANUFACTURE OF SAME

RELATED APPLICATIONS

This is a continuation-in-part application under 37 C.F.R. §1.53 of application Ser. No. 08/474,378 filed Jun. 7, 1995, now abandoned.

TECHNICAL FIELD

The present invention relates generally to the manufacture of shoes and socks and, in particular, to shoes having a fabric lining including an anti-microbial agent for inhibiting the growth of bacteria, fungus, viruses etc., and to sock liners including an anti-microbial agent for inhibiting the growth of bacteria, fungus, viruses etc.

BACKGROUND OF THE INVENTION

Odor caused by bacteria and other microbes including fungi and viruses are common problems associated with shoes in general and athletic shoes in particular. Scented powders have been used to mask foot odor; however, such powders typically do not destroy the microbes causing the odor or prevent them from multiplying. Medicated powders and foot rubs may attack foot fungus or bacteria but are inconvenient to use as they must be applied directly to the foot.

U.S. Pat. No. 4,935,061 discloses urethane shoe inserts having anti-microbial properties. U.S. Pat. No. 5,114,984 discloses a method for incorporating the biocide and fungicide zinc OMADINE® manufactured by the Olin Corporation into urethane. However, urethane shoe inserts may slip and wad up during use.

Many shoes, athletic shoes in particular, often have cloth linings or synthetic simulated leather linings.
The present invention meets the need of incorporating an anti-microbial agent directly into shoe linings or alternatively into a sock liner.

SUMMARY OF THE INVENTION

The present invention comprises shoe linings and sock liners including an anti-microbial agent for inhibiting the growth of bacteria, fungus and other microbes and the method of manufacture of same. A microbial inhibitor is blended in concentrations and quantities determined by the desired microbial inhibition range of the finished product with a thermoplastic resin such as polypropylene or polyethylene in predetermined quantities based on the desired flowability and melt properties of an anti-microbial resin feedstock. The anti-microbial feedstock is then used in forming anti-microbial product. The anti-microbial additive is mixed evenly throughout the polymeric material and migrates to the surface of the finished product on demand.

The present invention provides protection against odor and foot infections caused by bacteria fungi and other microbes residing within shoes. Additionally, the present invention inhibits the growth of unsightly mildew on the linings of shoes.

BRIEF DESCRIPTION OF THE DRAWINGS

A more complete understanding of the invention may be had by reference to the following Detailed Description when taken in conjunction with the accompanying Drawings in which.

DETAILED DESCRIPTION

This application is a continuation-in-part application of U.S. application Ser. No. 08/474,378 filed Jun. 7, 1995, now abandoned said application being fully incorporated herein by reference as if it has been fully set forth as text herein. As used herein the term "microbial" includes bacteria, viruses, fungi and other microbes.

Figures 1, 2, 3, 4:
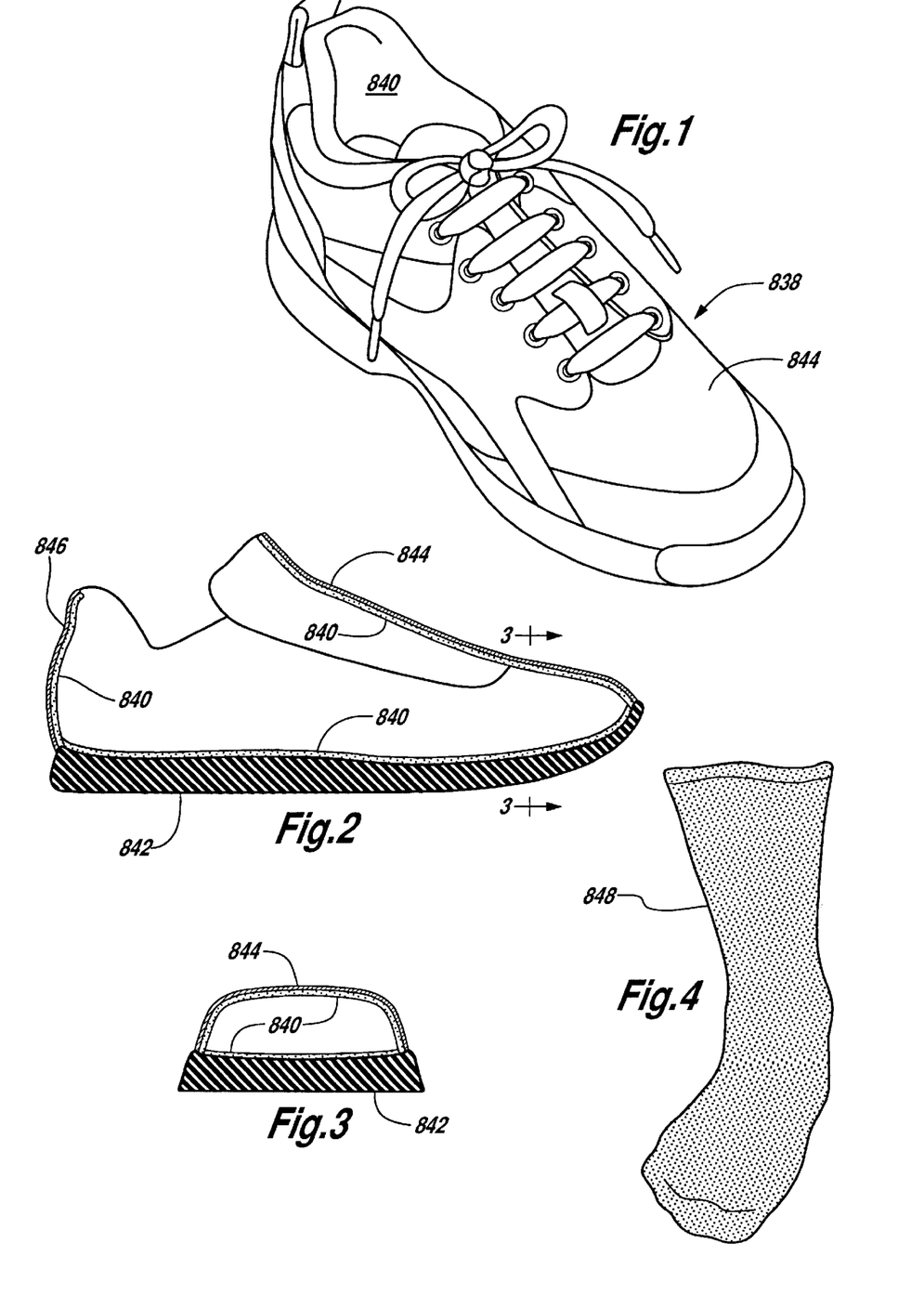
FIG. 1 is a perspective view of a shoe having a lining of the present invention incorporating an anti-microbial agent.
FIG. 2 is a longitudinal cross section of the shoe and lining of FIG. 1.
FIG. 3 is a lateral cross section of the shoe and lining of FIG. 1.
FIG. 4 is a perspective of a sock liner of the present invention incorporating an anti-microbial agent.

Referring now to FIG. 1, therein is illustrated a perspective view of a shoe 838 having a lining 840 of the present invention incorporating an anti-microbial agent. Referring to FIGS. 2 and 3, therein is illustrated the shoe 838 including a sole 842, a body 844, a heel section 846 and the lining 840. The lining 840 may cover substantially all of the interior of the shoe as illustrated in FIGS. 2 and 3 or only a portion thereof. The present invention meets the need of incorporating anti-microbial agent directly into the lining of the shoe instead of incorporating the anti-microbial agent in insert pads or powders. The present invention provides protection against odor and foot infections caused by bacteria, fungi and other microbes residing in the inside of shoes. Additionally, the present invention inhibits the growth of unsightly mildew on the linings of shoes. The shoe lining 840 may be made from any of the alternative fabric compositions and manufacturing methods disclosed hereinafter.

Referring to FIG. 4, therein is illustrated an alternate embodiment of the present invention comprising a sock liner 848 incorporating an anti-microbial agent. Sock liners have the same appearance and configuration as socks but are typically quite thin in construction. Sock liners are used inside heavy socks which are in turn used with shoes, ski boots and hiking boots etc. A sock liner is typically knitted or woven from a polypropylene based fabric, which wicks moisture away from the foot into the surrounding exterior sock, thereby keeping the foot dry. Keeping the foot dry reduces the likelihood of blisters and discomfort due to cold.

The use of the present invention is particularly advantageous in conjunction with athletic shoe, sock liners, and in similar applications. For example, due to their construction, it is often not practical to wash and dry athletic shoes in a manner that would kill microbes. Similarly, during hiking, hunting, fishing, and similar activities it may not be possible to properly wash sock liners between uses. By means of the present invention bacteria, fungi, and other microbes are prevented form growing in and on the interiors of athletic shoes, in and on sock liners, etc.

Figure 5A:
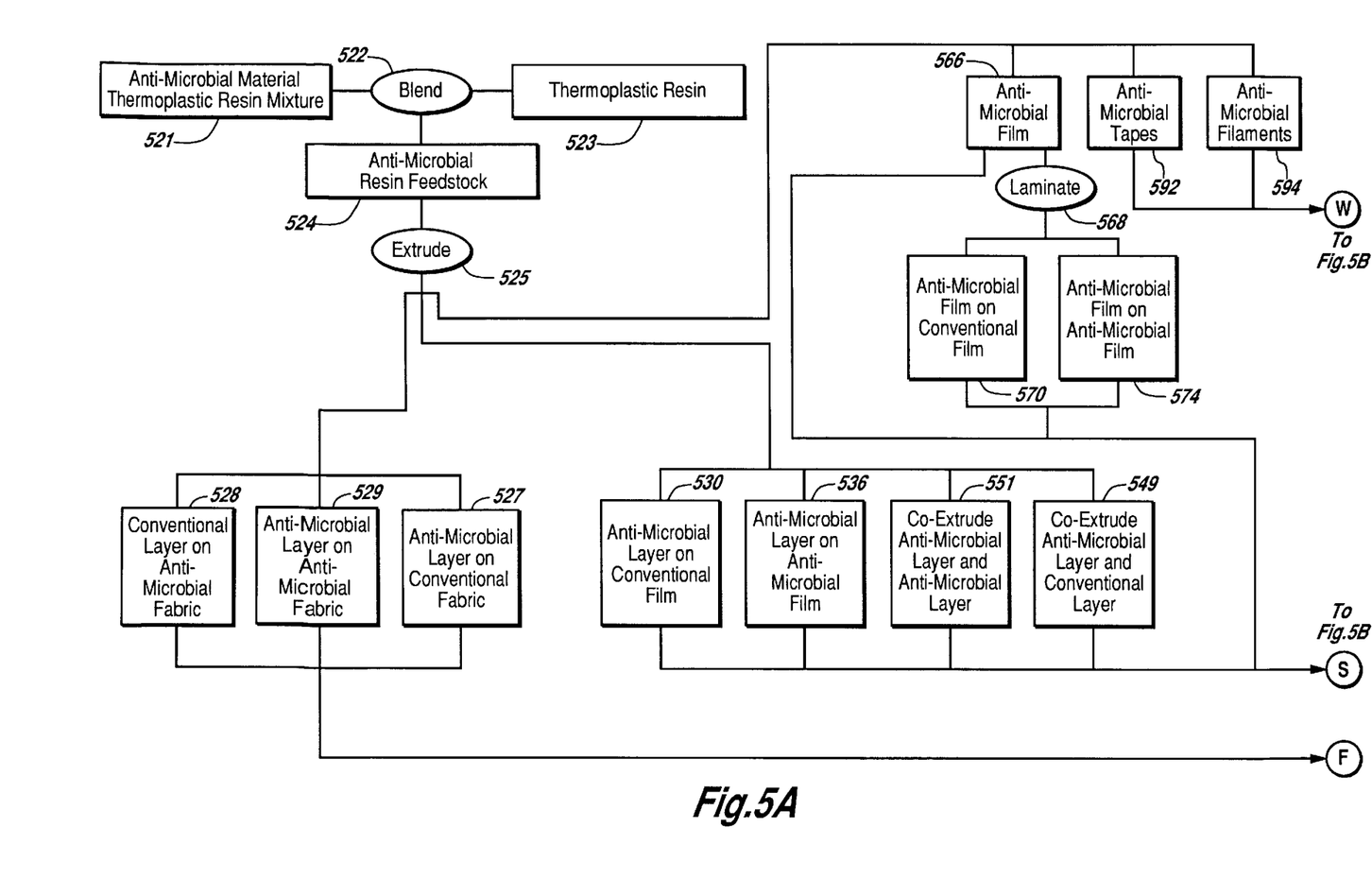
FIGS. 5A, 5B, and 5C comprise a flow chart illustrating numerous alternative methods for producing fabric for shoe lining and sock liners incorporating improved microbial inhibition.
Figures 5B, 8:
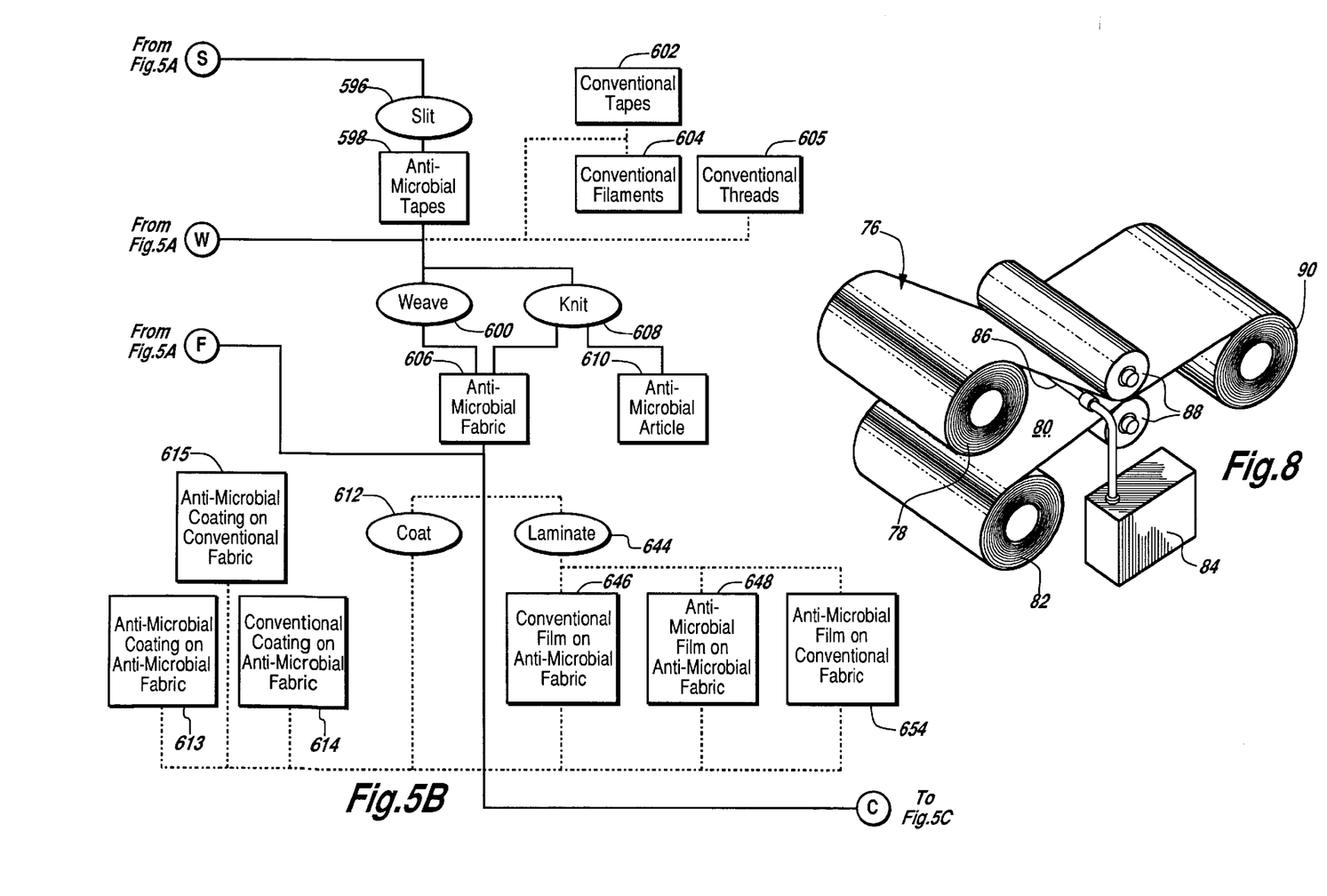
FIG. 8 is a diagrammatic illustration of a lamination apparatus and process.
Figures 5C, 6:
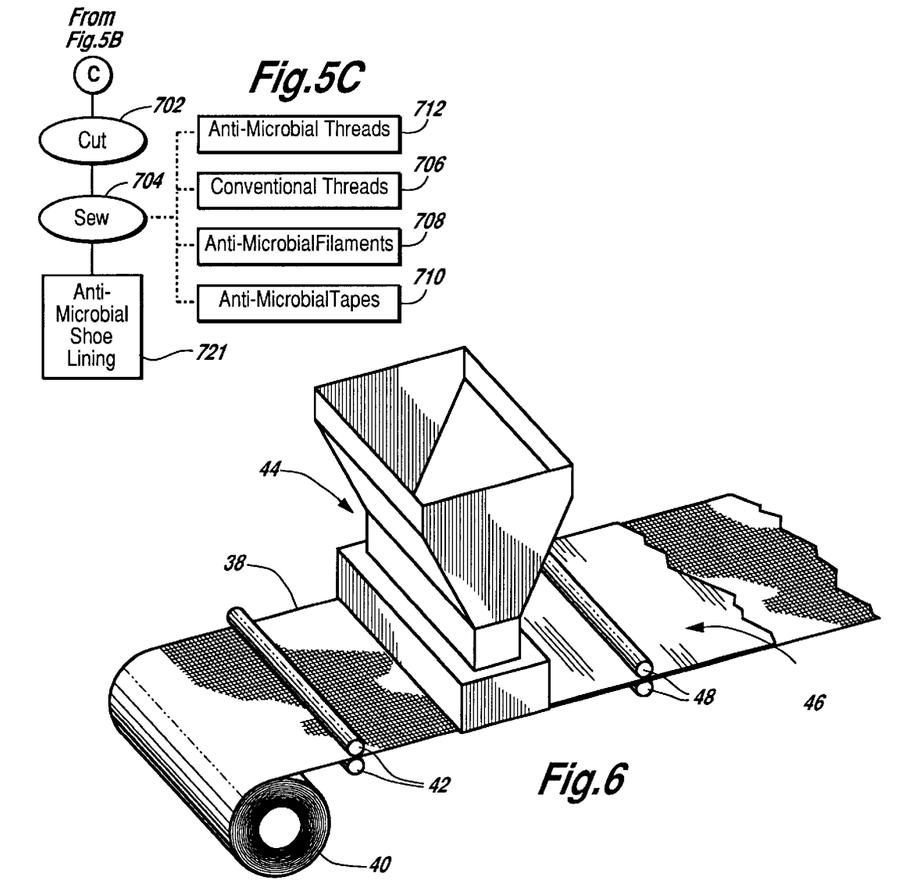
FIG. 6 is a diagrammatic illustration of an extruder.

Referring now to FIGS. 5A, 5B and 5C, therein is a flow chart illustrating the use of the present invention in the manufacture of anti-microbial products. Referring to FIG. 5A, an anti-microbial material/mixture 521 is pre-compounded. The mixture 521 may include a bactericide/fungicide agent of the type manufactured by Olin Chemical at 350 Knotter Drive, Cheshire Conn., 06410, under the trade name zinc Omadine®. The agent is marketed by Olin Corporation in a 95 percent powder form under EPA registration number 1258-840. The agent is insoluble in water. The agent is compounded with milled polypropylene or milled polyethylene to an agent concentration of approximately 7000 ppm. The agent is capable of inhibiting the growth of algae, mold, mildew and bacteria including E-Coli and Salmonella, as well as other microorganisms. Zinc Omadine® bactericide-fungicide is a derivative of pyrithione. Pyrithione is known by any of several names:

2-mercaptopyridine-N-oxide

1-hydroxpyridine-2-thione 2-pyridinethiol-1-oxide (CAS No. 1121-31-9)

1-hydroxy-2(1H)-pyridinethione (CAS No. 121-30-8)

The zinc derivative is a chelated complex as shown below:

Structural Formula

Zinc 2-pyridinethiol-1-oxide,
($c_{10}H_8N_2O_2S_2Zn$)

Zinc Omadine® bactericide-fungicide is listed in the *CTFA International Cosmetic Ingredient Dictionary*, 4th Edition, as zinc pyrithione. In the *Chemical Abstracts Registry*, zinc pyrithione is listed as:

bis[1-hydroxy-2(1H)-pyridinethionato-0,S]-(T-4) zinc (CAS No. 13463-41-7).

Typical physical properties are shown in Table 1. Solubility in a variety of solvents is shown in Table 2.

TABLE 1

Typical Physical Properties

| | Powder | 48% Standard Dispersion | 48% Fine Particle Dispersion |
|---|---|---|---|
| Molecular Weight | 317.7 | — | — |
| Assay, % | 95–99 | 48–50 | 48–50 |
| Color | off-white | off-white | off-white |
| Odor | mild | mild | mild |
| Specific Gravity @ 25° C. | 1.782 | — | — |
| Density (lb/gal) | — | 10 | 10 |
| Bulk Density (g/ml) | 0.35 | — | — |
| pH, 5% in water, average | 6.5–8.5 | 6.5–8.5 | 6.5–8.5 |
| Melting Point, ° C. (decomposes) | ~240 | — | — |
| Particle Size, % | 70 < 25μ (wet sieve) | 90 < 5μ | 901μ |

TABLE 2

Solubility$^a$ (w/w % at 25° C.)

| Solvent | Zinc Omadine ® bactericide-fungicide |
|---|---|
| Water, pH 7 | 0.0008 |
| Ethanol, 40A | 0.01 |
| Isopropanol | 0.008 |
| Propylene glycol | 0.02 |
| Polyethylene glycol 400 | 0.2 |
| Ethyleneglycol monomethyl ether | 0.09 |
| Diethyleneglycol monoethyl ether | 0.01 |
| Chloroform | 0.3 |
| Dimethylsulfoxide | 4 |
| Mineral oil, light | <0.0001 |
| Olive oil | <0.0003 |

TABLE 2-continued

Solubility[a] (w/w % at 25° C.)

| Solvent | Zinc Omadine ® bactericide-fungicide |
|---|---|
| Castor oil | <0.0001 |
| Isopropyl myristate | <0.0001 |
| Isopropyl palmitate | <0.0001 |

[a]Average solubility of technical grade material

Antimicrobial Activity

The Minimum Inhibitory Concentrations (MIC) listed in Table 3 show that, in vitro, very low concentrations of zinc Omadine® bactericide-fungicide inhibit many microorganisms, indicative of its broad spectrum of activity. In general the MIC of zinc Omadine® antimicrobial agent in vitro are less than 50 ppm for most bacteria, less than 5 ppm for most fungi (molds and yeasts), and less than 1 ppm for most algae. However, like all antimicrobial agents, higher concentrations than the MIC values may be required for adequate effectiveness in formulated products. This is due to the many variables (e.g. components in the formulation and fluctuating levels of microorganisms) which affect antimicrobial activity. Therefore, Olin's application data sheets should be consulted to determine the recommended use levels of zinc Omadine® bactericide-fungicide.

Chemical Properties

Unless otherwise noted, the following chemical properties refer to the commercial product and are typical values, not specifications.

Heat Stability. Zinc Omadine® biocide is stable at 100° C. for at least 120 hours. The decomposition temperature is 240° C.

TABLE 3

Antimicrobial Activity[1]
Minimum Inhibitory Concentrations[2]
Micrograms/ml (ppm)

| Organism | ATCC No. | Zinc Omadine ®[3] bactericide-fungicide |
|---|---|---|
| Gram Positive Bacteria | | |
| Staphylococcus aureus | 6538 | 4 |
| Streptococcus faecalis | 19433 | 16 |
| Gram Negative Bacteria | | |
| Escherichia coli | 9637 | 8 |
| Pseudomonas aeruginosa | 9721 | 512 |
| Klebsiella pheumoniae | 4352 | 8 |
| Molds | — | |
| Fusarium sp. | — | 32 |
| Aspergillus niger | 9542 | 8 |
| Aureobasidium pullulans | 9348 | ≦2 |
| Chaetomium globosum | 6205 | ≦2 |
| Gliocladium virens | 9645 | 64 |
| Penicillium pinophilum | 9644 | ≦2 |
| Yeasts | | |
| Candida Albicans | 11651 | ≦2 |
| Pityrosporum Ovale | — | 4 |
| Actinomycete | | |
| Streptoverticillium reticulum | 25607 | 4 |

TABLE 3-continued

Antimicrobial Activity[1]
Minimum Inhibitory Concentrations[2]
Micrograms/ml (ppm)

| Organism | ATCC No. | Zinc Omadine ®[3] bactericide-fungicide |
|---|---|---|
| Algae | | |
| Trentopholia odorata | — | ≦0.06 |
| Anacystis montana | — | ≦0.06 |
| Chloroccum tetrasponim | — | 8 |
| Sctonema hofmaannii | — | 0.5 |
| Synechocystis minima | — | ≦0.06 |

[1]Obtained by using 2-fold serial dilutions in microtiter plates. Bacterial concentrations were approximately $10^6$ organisms/ml. Fungal spore concentrations were approximately $10^5$ colony-forming units/ml.
[2]Lowest concentrations exerting a static effect on the microorganism.
[3]Because of the low solubility of zinc Omadine ® bactericide-fungicide in water, dimethylsulfoxide was used as a cosolvent.

The heat of decomposition, as measured under nitrogen by differential scanning calorimetry, is 150 cal/g.

pH Stability. Zinc Omadine® bactericide-fungicide can be used over the pH range from 4.5 to 9.5.

Alternatively, the anti-microbial agent used in the mixture of box 521 may be of the type distributed by The Microban Products Company of Huntersville, N.C. and identified by the trademark MICROBAN® or IRGASAN DP 300® manufactured by Ciba Geigy.

Referring particularly to boxes 521, 522, 523, and 524 of FIG. 5A, the anti-microbial material/thermoplastic resin mixture of box 521 resulting from the compounding step is blended with a thermoplastic resin to form an anti-microbial resin feedstock.

The anti-microbial material/thermoplastic resin mixture of box 521 is blended with the thermoplastic resin of box 523 in conventional blending equipment to provide the anti-microbial feedstock of box 524 having anti-microbial characteristics. The particular thermoplastic resin of box 523 which is selected for blending with the anti-microbial material/thermoplastic resin mixture of box 521 is preferably of the same general type as the resin comprising the anti-microbial material/thermoplastic resin mixture, and is selected in accordance with the desired melt temperature and the desired melt flow rate utilizing prior art techniques. Polypropylene is typically used for producing the fabric products of the present invention.

In the case of the anti-microbial agent zinc Omadine®, the concentration is maintained at about 4000 ppm. Due to thermal degradation in the process of blending and extrusion the active level of zinc Omadine® in the end product may be below 4000 ppm.

Referring to box 525, the next step in the practice of the invention comprises the extrusion of the anti-microbial resin feedstock from box 524 to form any one of a variety of products. For example, the extrusion step may be used to form an anti-microbial layer on a conventional fabric as indicated at box 527, or to form an anti-microbial layer on an anti-microbial fabric as indicated at box 529, or to form a layer of conventional polymeric material on an anti-microbial fabric 528. The extrusion step may also be used to form an anti-microbial layer on a conventional polymeric film as indicated at box 530, or to form an anti-microbial layer on an anti-microbial film as indicated at box 536. The procedures of boxes 527, 529, 530, and 536 may be carried out as illustrated in FIG. 6.

A length of material 38, which may comprise anti-microbial or conventional fabric or anti-microbial or conventional film, is fed from a supply roll 40 by means of pinch rollers 42 or other conventional apparatus. The length of material 38 extends through an extruder 44 which extrudes a layer of anti-microbial material 46 onto the length of material 38. The thickness of the layer of anti-microbial material 46 on the length of the material 38 is controlled by the operation of the extruder 44 and by the operation of a pair of pinch rollers 48 or other conventional apparatus typically employed in extrusion processes.

Figure 7:
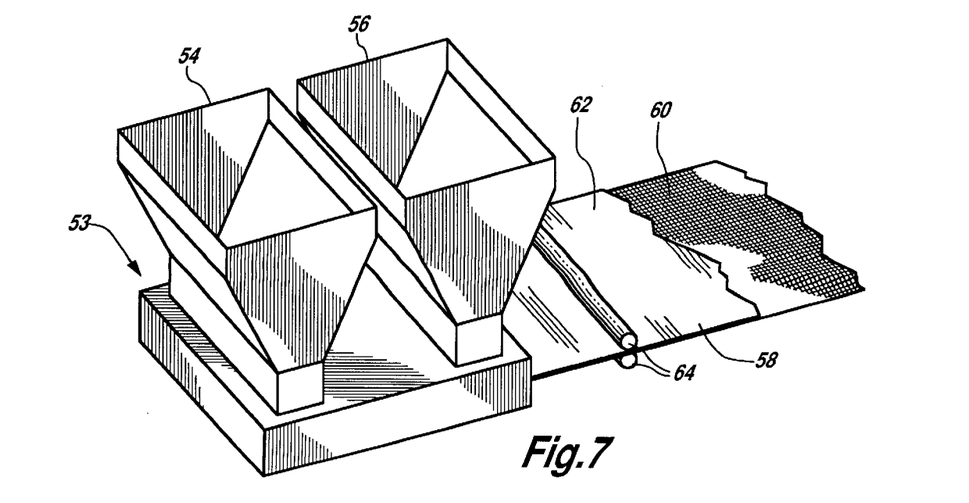
FIG. 7 is a diagrammatic illustration of a co-extruder.

Another important aspect of the invention is indicated at boxes 549 and 551 of FIG. 5A and illustrated in FIG. 7. An anti-microbial layer may be co-extruded with a layer of conventional polymeric film or with another anti-microbial layer to provide a co-extruded film useful in the practice of the invention.

As illustrated in FIG. 7, a conventional co-extrusion apparatus 53 comprises a hopper 54 which receives either an anti-microbial resin or a conventional thermoplastic resin and a hopper 56 which receives the anti-microbial resin feedstock of box 524 of FIG. 5A. The co-extrusion apparatus 53 is utilized to form a length of material 58 comprising either an anti-microbial layer or a conventional layer 60 and a co-extruded anti-microbial layer 62. The thickness of the length of material 58 and the layers 60 and 62 thereof is controlled by the operation of the co-extrusion apparatus 53 and by the operation of a pair of pinch rollers 64 and/or other conventional apparatus typically used in co-extrusion procedures. Typically, the anti-microbial layer 62 will be thinner than the layer 60 for purposes of economy.

Referring again to FIG. 5A, the extrusion step of box 525 may be utilized to form a variety of anti-microbial members, including anti-microbial tapes, anti-microbial filaments and anti-microbial film as indicated at box 566. The anti-microbial film of box 566 may be utilized directly in subsequent steps of the invention or as indicated at box 568, the anti-microbial film may be used in the furtherance of lamination procedures also comprising an important aspect of the invention. Specifically, the anti-microbial film of box 566 may be laminated onto a conventional film as indicated at box 570 onto an anti-microbial film as indicated at box 574. The foregoing procedures are further illustrated in FIG. 8. A length of anti-microbial film 76 may be fed from a feed roll 78. A length of material 80, comprising either a conventional film or an anti-microbial film, is fed from a supply roll 82. A reservoir 84 contains a supply of liquid adhesive, which is preferably a thermoplastic adhesive matched to the materials comprising the length of material 76 and the length of material 80. Liquid adhesive is fed from the reservoir 84 to a nozzle 86 located between the lengths of material 76 and 80 and used to apply liquid adhesive thereto. Immediately after the application of liquid adhesive thereto, the lengths of material 76 and 80 are fed between a pair of pinch rollers 88, whereby the length a material is securely bonded to the length of material 80 under the action of the liquid adhesive dispensed from the nozzle 86. The resulting laminate may be wound upon a take-up roll 90 or utilized directly.

Referring again to FIG. 5A, the extrusion step of box 525 may be used to form anti-microbial tapes as indicated at box 592. The anti-microbial tapes are not entirely unlike the anti-microbial film of box 566, but differ therefrom dimensionally. Whereas the anti-microbial film of box 566 is typically long and wide and characterized by a substantial thickness, the anti-microbial tapes of box 592 are typically relatively long, relatively narrow, relatively thin, and flat in cross section. The anti-microbial tapes of box 592 are dimensionally similar to the polymeric tapes which are conventionally supplied for use in weaving fabrics to be used in the manufacture of flexible, collapsible containers for flowable materials.

As indicated at box 594, the extrusion process of box 525 may also be used to manufacture anti-microbial filaments. The anti-microbial filaments of box 594 are similar to the anti-microbial tapes of box 592 in that they comprise weavable members which may be utilized in a conventional weaving apparatus to manufacture fabrics which may in turn be used in the manufacture of flexible, collapsible bags for handling flowable materials. The anti-microbial filaments of box 594 differ from the anti-microbial tapes of box 592 in that, whereas the anti-microbial tapes are typically flat in cross section, the anti-microbial filaments of box 594 are typically round or oval in cross section and therefor resemble conventional threads. The anti-microbial filaments 594 are typically extruded in 600 to 1000 denier fineness. Additionally, the filaments 594 may be extruded through a spineret that extrudes a multifilament fiber that is spun together as it is extruded. The anti-microbial tapes of box 592 and/or the anti-microbial filaments of box 594 may be twisted to form anti-microbial threads, if desired.

The anti-microbial tapes of box 592 may conveniently be thought of as extruded anti-microbial tapes comprising weavable members useful in a conventional weaving apparatus to form an anti-microbial fabric. As indicated by box 596 of FIG. 5B, the anti-microbial layers extruded onto the various films of boxes 530 and 536, the anti-microbial layers co-extruded with the various layers of boxes 549 and 551; the anti-microbial film of box 566, and/or the anti-microbial films laminated onto the various films of boxes 570 and 574 may also be utilized to form anti-microbial tapes by means of conventional slitting apparatus. Like the anti-microbial tapes of box 592, the anti-microbial tapes formed in the slitting process of box 596 typically comprise a relatively long, relatively narrow, relatively thin configuration which is flat in cross section. The anti-microbial tapes manufactured by the slitting step of box 596 may be conveniently considered as slit anti-microbial tapes as compared with the extruded anti-microbial tapes of box 592.

Referring to box 600, the next step in the practice of the invention comprises weaving one or more of the weavable members formed in accordance with the present invention and comprising the slit anti-microbial tapes of box 598, the extruded anti-microbial tapes of box 592, the extruded anti-microbial filaments of box 594 and/or anti-microbial threads to manufacture an anti-microbial fabric. As is indicated at boxes 602, 604, and 605 conventional tapes, and/or conventional filaments and/or conventional threads formed from non-anti-microbial polymeric materials may be combined with the weavable anti-microbial members of the present invention to form an anti-microbial fabric, if desired. In such event, the weavable anti-microbial members of the present invention would typically comprise a reduced proportion of the total number of weavable members utilized in the weaving step of box 600 to form an anti-microbial fabric and typically would be arranged in a grid pattern. Alternatively, the anti-microbial tapes and/or threads of the present invention may be twisted together with conventional tapes or filaments to form anti-microbial threads which may be used in the weaving step.

As indicated at box 606, the results of the weaving step of box 600 is anti-microbial fabric.

Referring to box 608, the anti-microbial materials of the present invention, whether singly, in combination with other anti-microbial materials of the present invention or in combination with conventional tapes and/or filaments, may be utilized in the knitting of anti-microbial fabric, or as indicated at box 610, anti-microbial articles. The knitting step of box 608 is useful when the resulting article does not require dimensional stability. The knitted sock liner 848 as illustrated in FIG. 4 is one such application of knitting.

Referring now to FIG. 5B and particularly to box 612, the next step in the practice of the invention may optionally comprise the coating of the anti-microbial fabric of box 606 with an anti-microbial material to provide an anti-microbial coating on an anti-microbial fabric as indicated at box 613. The anti-microbial fabric may also be coated with a conventional coating as indicated at box 614. The coating step may also be used to apply a layer of anti-microbial material to a conventional polymeric fabric as indicated at box 615. The coating step of 612 may be carried out utilizing various conventional procedures, as shown in FIGS. 12 and 13.

Figures 12, 13:
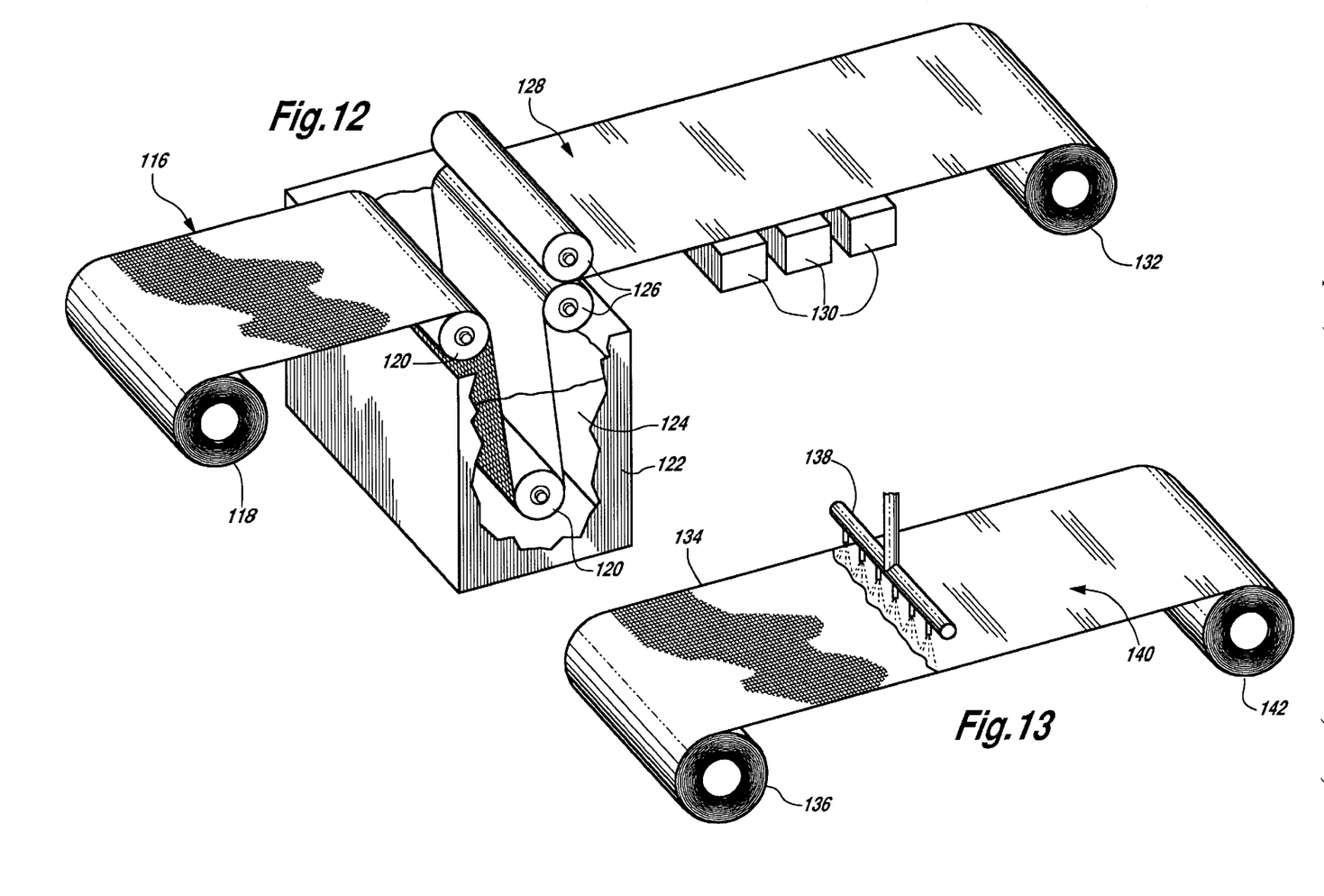
FIG. 12 is a diagrammatic illustration of a dip coating apparatus and process.
FIG. 13 is a diagrammatic illustration of a spray coating apparatus and process.

Referring specifically to FIG. 12, a length of anti-static material 116 manufactured in accordance with the present invention is fed from a supply roll 118 and is directed over rollers 120 and through a vat 122 having a quantity of liquid anti-microbial material 124 contained therein. The length of material 116 then passes between a pair of pinch rollers 126 which function to remove excess liquid anti-microbial material from the length of material 116. The length of anti-microbial material 116 having the coating of anti-microbial material 128 coated thereon then passes adjacent a plurality of driers 130 which function to solidify the coating of anti-microbial material 128 on the length of anti-microbial material 116 which is then accumulated on a take-up roll 132 or utilized directly.

An alternative coating procedure is illustrated in FIG. 13. A length of anti-microbial material 134 is fed from a supply roll 136. The length of anti-microbial material 134 passes under a conventional spray head 138 which functions to deposit a coating of anti-microbial material 140 on the length of anti-microbial material 134. The coating dries in the atmosphere and the length of anti-microbial material having the anti-microbial coating 140 formed thereon is then accumulated on a take-up roll 142 or utilized directly.

The coating procedures of FIGS. 12 and 13 are not limited to the application of anti-microbial material to anti-microbial fabric. As indicated at box 615, the procedures of FIGS. 12 and 13 and other conventional coating procedures can be used to apply the anti-microbial material of the present invention to conventional fabrics. An optional laminating step comprising the present invention is also illustrated in FIG. 5B at box 644. The laminating step may be carried out as described hereinabove in connection with FIG. 8, and may be used to laminate a conventional film onto an anti-microbial fabric as indicated at box 646 or to laminate an anti-microbial film onto an anti-microbial fabric as indicated at box 648, or to laminate an anti-microbial film onto a conventional fabric as indicated at box 654. The anti-microbial film may be manufactured in accordance with the invention by the extrusion process of box 525 of FIG. 5A to provide the anti-microbial film of box 566. The laminating process may be carried out in accordance with the procedure described in accordance with FIG. 8.

Figure 9A:
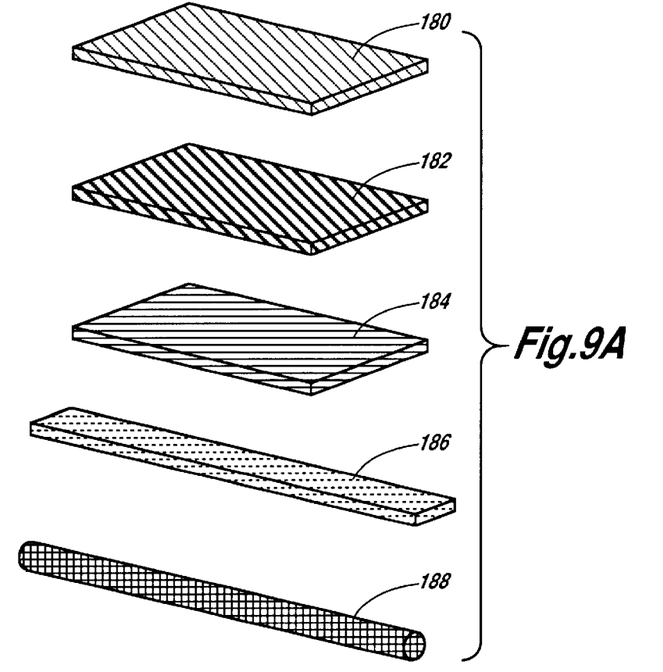
FIGS. 9A and 9B comprise a key useful in interpreting FIGS. 10A–10I and FIGS. 11A–11E.
Figure 9B:
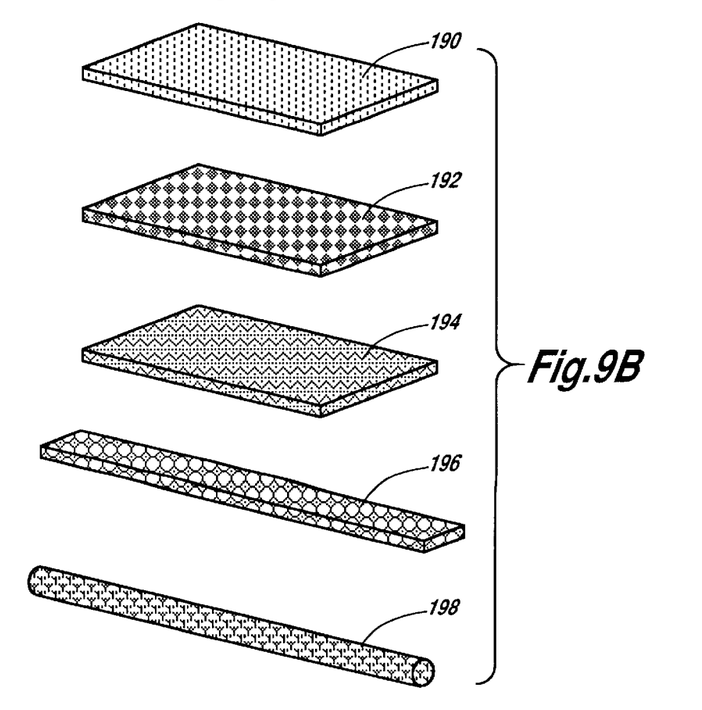

The results of the foregoing steps comprising the present invention are illustrated in FIGS. 9A and 9B, inclusive; FIGS. 10A through 10I, inclusive; and FIGS. 11A through 11E, inclusive. Referring first to FIG. 9A, therein is illustrated an anti-microbial layer 180, an anti-microbial fabric 182, an anti-microbial film 184, an anti-microbial tape 186, and an anti-microbial filament 188. In FIG. 9B there is shown a conventional layer 190, a conventional fabric 192, a conventional film 194, a conventional tape 196, and a conventional filament 198.

Figure 10A:
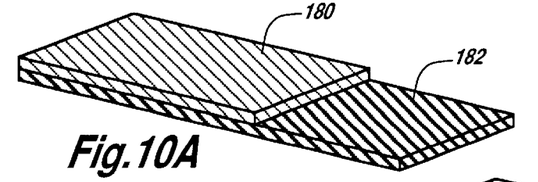
FIG. 10A is a perspective view of an anti-microbial layer extruded onto an anti-microbial fabric.
Figure 10B:
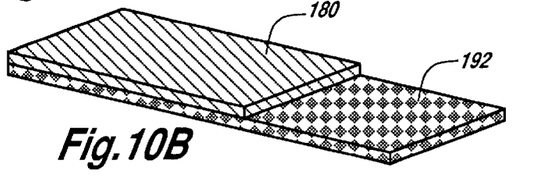
FIG. 10B is a perspective view of an anti-microbial layer extruded onto a conventional fabric.
Figure 10C:
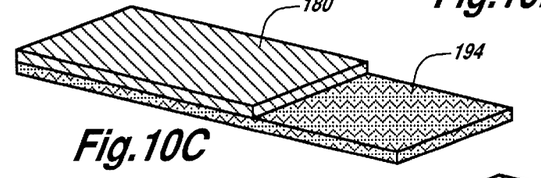
FIG. 10C is a perspective view of an anti-microbial layer extruded onto a conventional film.
Figure 10D:
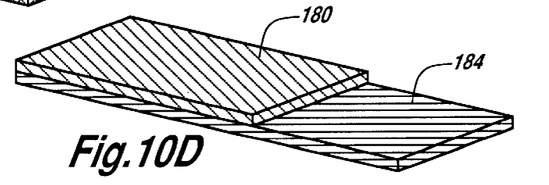
FIG. 10D is a perspective view of an anti-microbial layer extruded onto an anti-microbial film.

FIG. 10A comprises a perspective view of an anti-microbial layer 180 extruded onto an anti-microbial fabric 182 as indicated at box 529 of FIG. 5A. FIG. 10B is a perspective view of an anti-microbial layer 180 extruded onto a conventional fabric 192 as indicated at box 527. FIG. 10C is a perspective view of an anti-microbial layer 180 extruded onto a conventional film 194 as indicated at box 530. FIG. 10D is a perspective view of an anti-microbial layer extruded onto an anti-microbial film 184 as indicated at box 536.

Figure 10E:
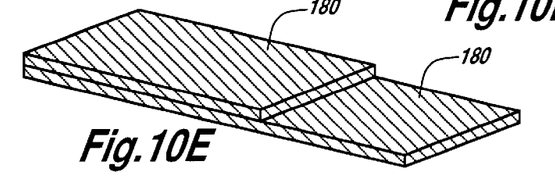
FIG. 10E is a perspective view of a co-extrusion comprising a layer of anti-microbial material and a layer of anti-microbial material.
Figures 10F, 10G, 10H, 10I:
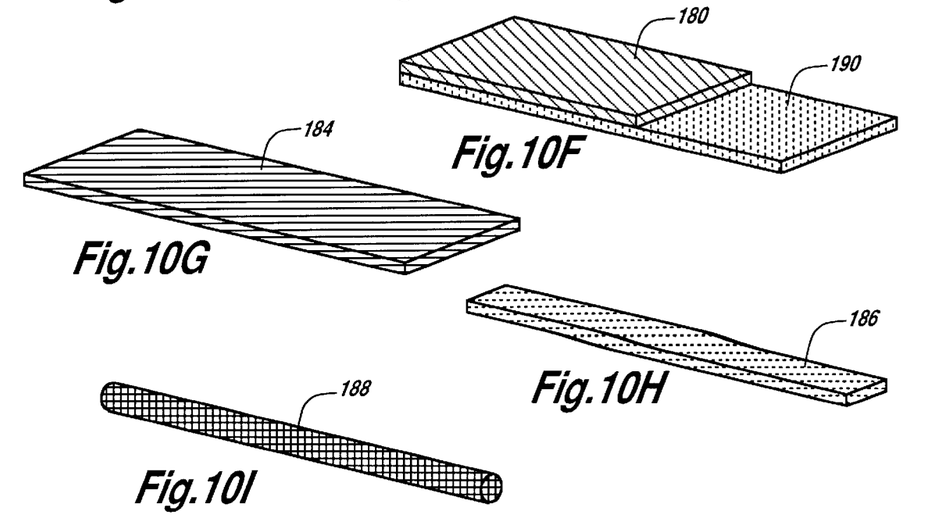
FIG. 10F is a perspective view of a co-extrusion comprising a layer of anti-microbial material and a layer of conventional polymeric material.
FIG. 10G is a perspective view of an extruded anti-microbial film.
FIG. 10H is a perspective view of an extruded anti-microbial tape.
FIG. 10I is a perspective view of an extruded anti-microbial filament.

FIG. 10E is a perspective view of an anti-microbial layer 180 co-extruded with an anti-microbial layer 180 as indicated at box 551. FIG. 10F is a perspective view of an anti-microbial layer 180 co-extruded with a conventional layer 190 as indicated at box 549. FIG. 10G is a perspective view of an anti-microbial film 184 as indicated at box 566. FIG. 10H is a perspective view of an anti-microbial tape 186 as indicated at box 592. FIG. 10I is a perspective view of an anti-microbial filament 188 as indicated at box 594.

Figure 11A:
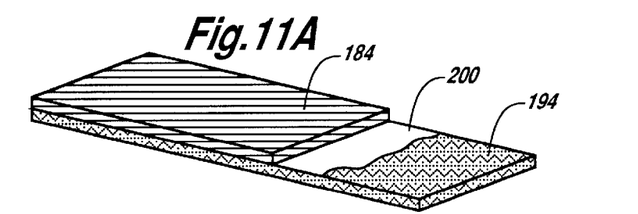
FIG. 11A is a perspective view of an anti-microbial film laminated onto an conventional film.
Figures 11B, 11C:
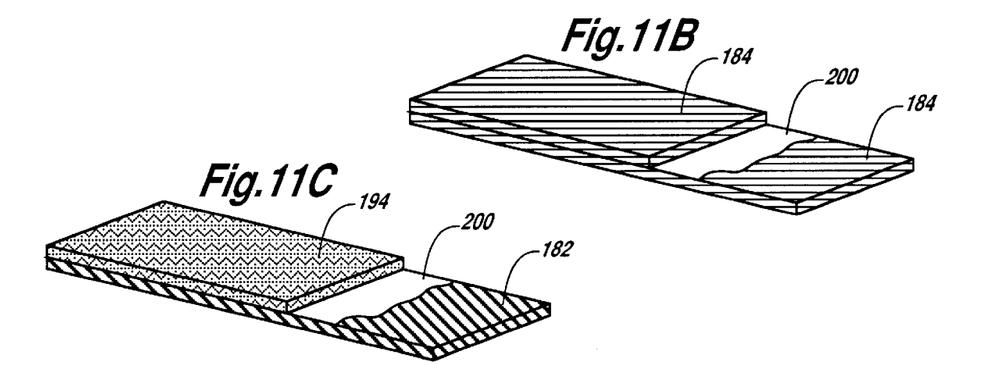
FIG. 11B is a perspective view of an anti-microbial film laminated onto an anti-microbial film.
FIG. 11C is a perspective view of a conventional polymeric film laminated onto an anti-microbial fabric.
Figure 11D:
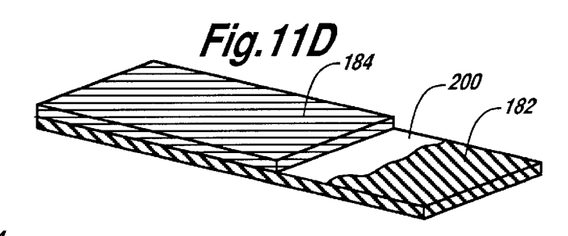
FIG. 11D is a perspective view of an anti-microbial film laminated onto an anti-microbial fabric.
Figure 11E:
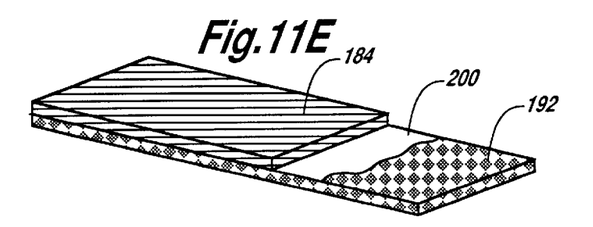
FIG. 11E is a perspective view of an anti-microbial film laminated onto a conventional film.

FIG. 11A is a perspective view of an anti-microbial film 184 laminated to a conventional film 194 by means of a layer of thermo-plastic adhesive 200 as indicated at box 570. FIG. 11B is a perspective view of an anti-microbial film 184 laminated to an anti-microbial film 184 by means of a layer of thermo-plastic adhesive 200 as indicated at box 574. FIG. 11C is a perspective view of a conventional film 194 laminated to an anti-microbial fabric 182 by means of a layer of thermoplastic adhesive 200 as indicated at box 646. FIG. 11D is a perspective view of an anti-microbial film 184 laminated to an anti-microbial fabric 182 by means of a layer of thermo-plastic adhesive 200 as indicated at box 648. FIG. 11E is a perspective view of an anti-microbial film 184 laminated to a conventional fabric 192 by means of a layer of thermo-plastic adhesive 200 as indicated at box 654.

As indicated at box 702 of FIG. 5C, the next step in the practice of the present invention comprises the cutting of the anti-microbial fabric in accordance with a predetermined pattern to provide the pieces necessary to fabricate an anti-microbial shoe lining at box 721. The cutting step of box 702 may be utilized in conjunction with the anti-microbial fabric of box 606; or with the fabrics comprising an anti-microbial layer extruded onto a fabric of boxes 527 or 529; or with a fabric having an anti-microbial coating thereon as depicted in boxes 613 and 615; or with a fabric having a film laminated thereon as depicted at boxes 646 and 648. In any event, the anti-microbial fabric is cut utilizing conventional fabric cutting apparatus and in accordance with a predetermined pattern to provide the pieces necessary to fabricate the desired shoe lining configuration at box 721.

The next step in the practice of the present invention comprises the sewing step of box 704. The sewing step of box 704 incorporates a variety of options. For example, the sewing step of the present invention may be carried out utilizing conventional threads as indicated at box 706. Alternatively, the sewing step may be carried out utilizing an anti-microbial filaments as indicated at box 708. The anti-microbial filaments of box 708 may be fabricated in accordance with the present invention as indicated at box 594 by utilizing conventional techniques. Still another alternative is the utilization of anti-microbial tapes in the sewing step of box 704 as indicated at box 710. Like the anti-microbial filaments of box 708, the anti-microbial tapes may be fabricated in accordance with the present invention either as indicated at box 592 or as indicated at box 598, or the anti-microbial tapes of box 710 may be fabricated utilizing conventional techniques. Anti-microbial threads may also be used as indicated at box 712. The anti-microbial additive in the above described films is mixed evenly throughout the polymeric material and migrates to the surface of the finished product on demand.

Although preferred embodiments of the invention have been illustrated in the accompanying Drawings as described in the foregoing Detailed Description, it will be understood that the invention is not limited to the embodiments disclosed, but is capable of numerous rearrangements, modifications, and substitutions of parts and elements without departing from the spirit of the invention.

We claim:

1. A method of manufacturing an anti-microbial shoe lining comprising the steps of:
   providing a quantity of a thermoplastic resin including an zinc pyrithione agent admixture having a predetermined microbial inhibition characteristic;
   blending the thermoplastic resin with a polymeric resin having predetermined physical characteristics to form an anti-microbial feedstock having a concentration of between 1000 and 4000 ppm of zinc pyrthione;
   extruding the anti-microbial feedstock into anti-microbial tapes comprising relatively long, narrow, thin lenghts of anti-microbial material;
   weaving the anti-microbial tapes into an anti-microbial fabric having predetermined microbial inhibition characteristics;
   cutting the anti-microbial fabric into a plurality of pieces in accordance with a predetermined pattern; and
   joining the pieces of anti-microbial fabric together thereby constructing the anti-microbial shoe lining.

2. The method of manufacturing the anti-microbial shoe lining of claim 1 wherein the steps of extruding the anti-microbial resin into anti-microbial tapes and weaving an anti-microbial fabric further comprise:
   extruding a plurality of first tapes having a first microbial inhibition characteristic;
   extruding a plurality of second anti-microbial tapes having a second microbial inhibition characteristic; and
   weaving the plurality of first tapes and the plurality of second tapes to form an anti-microbial fabric.

3. The method of manufacturing the anti-microbial shoe lining of claim 1 furher including the step of:
   extruding a layer of anti-microbial resin onto the previously woven anti-microbial fabric.

4. The method of manufacturing the anti-microbial shoe lining of claim 1 further including the step of coating the anti-microbial fabric with the anti-microbial resin prior to cutting and joining the anti-microbial fabric to form the anti-microbial shoe lining.

5. A method of manufacturing an anti-microbial shoe lining comprising the steps of:
   providing a quantity of a thermoplastic resin including an zinc pyrithione agent admixture having a predetermined microbial inhibition characteristic;
   blending the thermoplastic resin with a polymeric resin having predetermined physical characteristics to form an anti-microbial feedstock having a concentration of between 1000 and 4000 ppm of zinc pyrthione;
   extruding the anti-microbial feedstock into anti-microbial filaments;
   weaving the anti-microbial filaments into an anti-microbial fabric having predetermined microbial inhibition characteristics;
   cutting the anti-microbial fabric into a plurality of pieces in accordance with a predetermined pattern; and
   joining the pieces of anti-microbial fabric together thereby constructing the anti-microbial shoe lining.

6. The method of manufacturing the anti-microbial shoe lining of claim 5 wherein the steps of forming anti-microbial filaments and weaving an anti-microbial fabric further comprise:
   extruding a plurality of first filaments having a first microbial inhibition characteristic;
   extruding a plurality of second anti-microbial filaments having a second microbial inhibition characteristic; and
   weaving the anti-microbial filaments to form an anti-microbial fabric.

7. A method of manufacturing an anti-microbial shoe lining comprising the steps of:
   providing a quantity of a thermoplastic resin including an zinc pyrithione agent admixture having a predetermined microbial inhibition characteristic;
   blending the thermoplastic resin with a polymeric resin having predetermined physical characteristics to form an anti-microbial feedstock having a concentration of between 1000 and 4000 ppm of zinc pyrthione;
   extruding the anti-microbial feedstock into an anti-microbial film;
   slitting the anti-microbial film into anti-microbial tapes comprising relatively long, narrow, thin lenghts of anti-microbial material;
   weaving the anti-microbial tapes into an anti-microbial fabric having predetermined microbial inhibition characteristics;
   cutting the anti-microbial fabric into a plurality of pieces in accordance with a predetermined pattern; and
   joining the pieces of anti-microbial fabric together thereby constructing the anti-microbial shoe lining.

8. A method of manufacturing an anti-microbial shoe lining comprising the steps of:
   providing a quantity of a thermoplastic resin including an zinc pyrithione agent admixture having a predetermined microbial inhibition characteristic;
   blending the thermoplastic resin with a polymeric resin having predetermined physical characteristics to form an anti-microbial feedstock having a concentration of between 1000 and 4000 ppm of zinc pyrthione;
   extruding a layer of anti-microbial resin onto a polymeric film to form an anti-microbial sheet;
   slitting the anti-microbial sheet into anti-microbial tapes comprising relatively long, narrow, thin lenghts of anti-microbial material;
   weaving the anti-microbial tapes into an anti-microbial fabric having predetermined microbial inhibition characteristics;
   cutting the anti-microbial fabric into a plurality of pieces in accordance with a predetermined pattern; and
   joining the pieces of anti-microbial fabric together thereby constructing the anti-microbial shoe lining.

9. A method of manufacturing an anti-microbial shoe lining comprising the steps of:
   providing a quantity of a thermoplastic resin including an zinc pyrithione agent admixture having a predetermined microbial inhibition characteristic;
   blending the thermoplastic resin with a polymeric resin having predetermined physical characteristics to form an anti-microbial feedstock having a concentration of between 1000 and 4000 ppm of zinc pyrthione;

co-extruding a layer of anti-microbial resin and a layer of a polymeric material to form an anti-microbial sheet;

slitting the anti-microbial sheet into anti-microbial tapes comprising relatively long, narrow, thin lenghts of anti-microbial material;

weaving the anti-microbial tapes into an anti-microbial fabric having predetermined microbial inhibition characteristics;

cutting the anti-microbial fabric into a plurality of pieces in accordance with a predetermined pattern; and joining the pieces of anti-microbial fabric together thereby constructing the anti-microbial shoe lining.

10. A method of manufacturing an anti-microbial shoe lining comprising the steps of:

providing a quantity of a thermoplastic resin including an zinc pyrithione agent admixture having a predetermined microbial inhibition characteristic;

blending the thermoplastic resin with a polymeric resin having predetermined physical characteristics to form an anti-microbial feedstock having a concentration of between 1000 and 4000 ppm of zinc pyrthione;

extruding the anti-microbial resin into an anti-microbial film;

laminating a layer of the anti-microbial film onto a polymeric film using a thermoplastic resin as a bonding agent to form an anti-microbial sheet;

slitting the anti-microbial sheet into anti-microbial tapes comprising relatively long, narrow, thin lenghts of anti-microbial material;

weaving the anti-microbial tapes into an anti-microbial fabric having predetermined microbial inhibition characteristics;

cutting the anti-microbial fabric into a plurality of pieces in accordance with a predetermined pattern; and joining the pieces of anti-microbial fabric together thereby constructing the anti-microbial shoe lining.

11. A method of manufacturing an anti-microbial shoe lining comprising the steps of:

providing a quantity of a thermoplastic resin including an zinc pyrithione agent admixture having a predetermined microbial inhibition characteristic;

blending the thermoplastic resin with a polymeric resin having predetermined physical characteristics to form an anti-microbial feedstock having a concentration of between 1000 and 4000 ppm of zinc pyrthione;

extruding a layer of the anti-microbial feedstock onto a woven polymeric fabric to form a fabric with an anti-microbial coating;

cutting the fabric with anti-microbial coating into a plurality of pieces in accordance with a predetermined pattern; and joining the pieces of anti-microbial fabric together thereby constructing the anti-microbial shoe lining.

12. A method of manufacturing an anti-microbial sock liner comprising the steps of:

providing a quantity of a thermoplastic resin including an zinc pyrithione agent admixture having a predetermined microbial inhibition characteristic;

blending the thermoplastic resin with a polymeric resin having predetermined physical characteristics to form an anti-microbial feedstock having a concentration of between 1000 and 4000 ppm of zinc pyrthione;

extruding a layer of the anti-microbial feedstock onto a woven polymeric fabric to form a fabric with an anti-microbial coating;

cutting the fabric with anti-microbial coating into a plurality of pieces in accordance with a predetermined pattern; and joining the pieces of anti-microbial fabric together thereby constructing the anti-microbial sock liner.

* * * * *